(12) United States Patent
Miyashita et al.

(10) Patent No.: US 9,212,975 B2
(45) Date of Patent: Dec. 15, 2015

(54) COLLECTION UNIT

(75) Inventors: Noe Miyashita, Chiba (JP); Ryusuke Gotoda, Chiba (JP)

(73) Assignee: Hitachi, Ltd., Tokyo (JP)

( * ) Notice: Subject to any disclaimer, the term of this patent is extended or adjusted under 35 U.S.C. 154(b) by 521 days.

(21) Appl. No.: 13/634,917

(22) PCT Filed: Jan. 31, 2011

(86) PCT No.: PCT/JP2011/051883
§ 371 (c)(1),
(2), (4) Date: Sep. 14, 2012

(87) PCT Pub. No.: WO2011/118256
PCT Pub. Date: Sep. 29, 2011

(65) Prior Publication Data
US 2013/0000422 A1 Jan. 3, 2013

(30) Foreign Application Priority Data
Mar. 26, 2010 (JP) .................................. 2010-072059

(51) Int. Cl.
*G01N 1/22* (2006.01)
*G01N 35/00* (2006.01)

(52) U.S. Cl.
CPC ............ *G01N 1/2208* (2013.01); *G01N 1/2214* (2013.01); *G01N 2035/00356* (2013.01)

(58) Field of Classification Search
CPC . G01N 1/2208; G01N 1/2273; G01N 1/2214; G01N 1/2205; B01L 2200/026; B01L 3/502
USPC .................... 73/863.01, 863.02, 863.03, 864, 73/864.54, 863.21, 863.22, 863.23, 73/863.24, 28.01, 28.05, 28.04, 28.06, 73/31.01–31.03, 31.07
See application file for complete search history.

(56) References Cited

U.S. PATENT DOCUMENTS 6,565,638 B1 5/2003 Sugita et al.
6,692,953 B1 * 2/2004 Sugita et al. ............... 435/309.1
(Continued)

FOREIGN PATENT DOCUMENTS

JP 568300 9/1993
JP 11-155597 6/1999
(Continued)

OTHER PUBLICATIONS

JP Office Action of Appln. No. 2010-072059 dated Mar. 1, 2013 with English translation.
(Continued)

*Primary Examiner* — Daniel S Larkin
*Assistant Examiner* — Jamar Ray
(74) *Attorney, Agent, or Firm* — Jones Robb, PLLC

(57) ABSTRACT

A collection unit (80) includes: a collection carrier cartridge (82) formed, at its center, with a through hole (82$b$3) into which a nozzle for supplying hot water or ATP reagent is inserted including a carrier filling dish (82$b$), on an outer circumference of the through hole (82$b$3), to be filled with a collection carrier (90) for collecting floating bacteria in the air, and an upper lid (82$a$) on which the carrier filling dish (82$b$) is placed, formed with a protrusion to be inserted through the through hole (82$b$3); an impactor nozzle head (86) covering a surface of the collection carrier (90) and has a plurality of nozzle holes (87) facing the collection carrier (90) surface; and a fan (84) introducing air to the collection carrier surface through the nozzle holes (87). A velocity of the air passing through the nozzle holes (87) is 40 m/s to 50 m/s.

6 Claims, 13 Drawing Sheets

(56) References Cited

U.S. PATENT DOCUMENTS

| | | |
|---|---|---|
| 2003/0206826 A1 | 11/2003 | Stanley |
| 2008/0241871 A1 | 10/2008 | Okanojo et al. |
| 2009/0142785 A1 | 6/2009 | Osato et al. |
| 2011/0183371 A1 | 7/2011 | Noda et al. |

FOREIGN PATENT DOCUMENTS

| | | |
|---|---|---|
| JP | 2000-300246 | 10/2000 |
| JP | 2000-304663 | 11/2000 |
| JP | 2002-028590 | 1/2002 |
| JP | 2008-249628 | 10/2008 |
| JP | 2009-11265 | 1/2009 |
| JP | 2009-131186 | 6/2009 |
| JP | 2009-139115 | 6/2009 |
| JP | 2011-133444 A | 7/2011 |
| JP | 2011-145112 A | 7/2011 |
| WO | WO 2009/157510 A1 | 12/2009 |
| WO | WO 2010/045686 A1 | 4/2010 |

OTHER PUBLICATIONS

Singapore Search Report of Appln. No. 201207074-4 dated Jun. 25, 2013 in English.

Hideyuki Noda et al., APID/High-Sensitivity Microorganism Measurement Technique in Bio-Clean Room Indoor Environment.

* cited by examiner

COLLECTION UNIT

TECHNICAL FIELD

The present invention relates to a collection unit particularly applicable to a luminescence measuring apparatus which collects biological cells floating in the air on a collecting carrier and measures luminescence with ATP method.

BACKGROUND ART

In an environment where sterility and biological cleanliness are required, such as various clinical medicines, food factories, medicine manufacturing plants, and basic research setting, the number of microorganisms in the air (airborne bacteria) (viable bacterial number), falling bacteria, adhesive bacteria, and the like are counted. As a method of measuring airborne bacteria, an airborne bacteria sampler for collecting floating bacteria by natural fall of floating bacteria and by suctioning a certain amount of air are generally utilized to collect the floating bacteria.

In the above methods, floating bacteria are collected on a nutrient agar plate medium, cultured in an incubator for two to three days, and a number of colonies generated after the culture is counted as the number of viable bacteria. However, this method has a disadvantage that a long time is required to culture viable bacteria.

Meanwhile, as a method capable of measuring the number of microorganisms within a short time, there has been known a method of measuring ATP (Adenosine Triphosphate) being an intracellular component by a bioluminescence method and converting the measurement result to the number of microorganisms.

In the bioluminescence method, a luciferin-luciferase luminescence reaction is used, in which the ATP amount is calculated from the luminescence amount of light generated by mixing and reacting a luminescence reagent containing substrate luciferin and enzyme luciferase and a sample solution containing the ATP extracted from a cell of a microorganism, and the number of viable bacteria is calculated based on the ATP amount per a viable bacterium. The Patent Literature 1 discloses a kit used for measuring the number of viable bacteria using such a luminescence reaction.

In the method of measuring the number of viable bacteria using the kit disclosed in the Patent Literature 1, it is possible to achieve the assured effect in terms of reduction of measurement time. However, when ultra minute amount of viable bacteria is to be measured, a luminescence amount itself is minute. Therefore, there is a disadvantage of great influence of background luminescence caused by residual ATP, intrusion of ATP not to be measured, and the like, and thus good measurement accuracy cannot be obtained.

Meanwhile, Patent Literature 2 discloses a luminescence measurement apparatus which suppresses viable bacteria adhered to a nozzle for dispensing a reagent and the background luminescence derived from residual ATP and can perform luminescence measurement accurately and promptly.

According to the luminescence measurement apparatus disclosed in the Patent Literature 2, it is considered possible to perform luminescence measurement accurately and promptly even for luminescence measurement where ultra minute amount of viable bacteria is measured.

In association with the collection of floating bacteria, Patent Literature 3 discloses a collection unit which can perform the operation of collecting and testing microorganisms floating in the air easily and within a short time.

CITATION LIST

Patent Literature

Patent Literature 1: Japanese Patent Application Laid-Open No. 11-155597
Patent Literature 2: Japanese Patent Application Laid-Open No. 2008-249628
Patent Literature 3: Japanese Patent Application Laid-Open No. 2009-131186

SUMMARY OF INVENTION

Technical Problem

In order to easily bring a collection unit into a room where floating bacteria are to be collected, the size of the entire collection unit is required to be reduced. However since viable bacteria are impacted against a collection carrier and carried by the collection carrier in the collection unit, a flow rate of air inflowing to the collection unit is required to be increased to some extent. With size reduction of a movable portion, the flow rate of the air inflowing to the collection unit may be reduced, and thus the collection time may become longer.

Thus, an object of the present invention is to provide a collection unit using a collection carrier, which can efficiently collect floating bacteria in the air even if the size of the collection unit is reduced.

Solution to Problem

In order to achieve the above object, a collection unit includes: a collection carrier cartridge formed, at its center, with a through hole into which a nozzle for supplying hot water or ATP reagent is inserted including a carrier filling dish, on an outer circumference of the through hole, to be filled with a collection carrier for collecting floating bacteria in the air and an upper lid, on which the carrier filling dish is placed, formed with a protrusion to be inserted through the through hole; an impactor nozzle head which covers a surface of the collection carrier and has a plurality of nozzle holes facing the surface of the collection carrier; and a fan which introduces air to the surface of the collection carrier through the nozzle holes, wherein a velocity of the air passing through the nozzle holes is 40 m/s to 50 m/s.

According to the collection unit, among the nozzle holes, adjacent nozzle holes may be arranged in a zigzag pattern. Adjacent nozzle holes among the nozzle holes may be arranged to have their centers at the respective apexes of an equilateral triangle in plan view of the impactor nozzle head.

According to the collection unit, the nozzle holes may have a hole diameter of 0.6 mm, a hole pitch between the nozzle holes may be 2.6 mm, and a distance between a lower surface of the impactor nozzle head and a surface of the collection carrier may be 1.5 mm.

Advantageous Effects of Invention

According to the collection unit of the present invention having the above configuration, even if the size of the entire unit is reduced, the flow rate of air passing through the nozzle hole of the impactor nozzle head can be maintained at a

DESCRIPTION OF EMBODIMENTS

Hereinafter, an embodiment according to a collection unit of the present invention will be described in detail with reference to the accompanying drawings.

Figure 1:
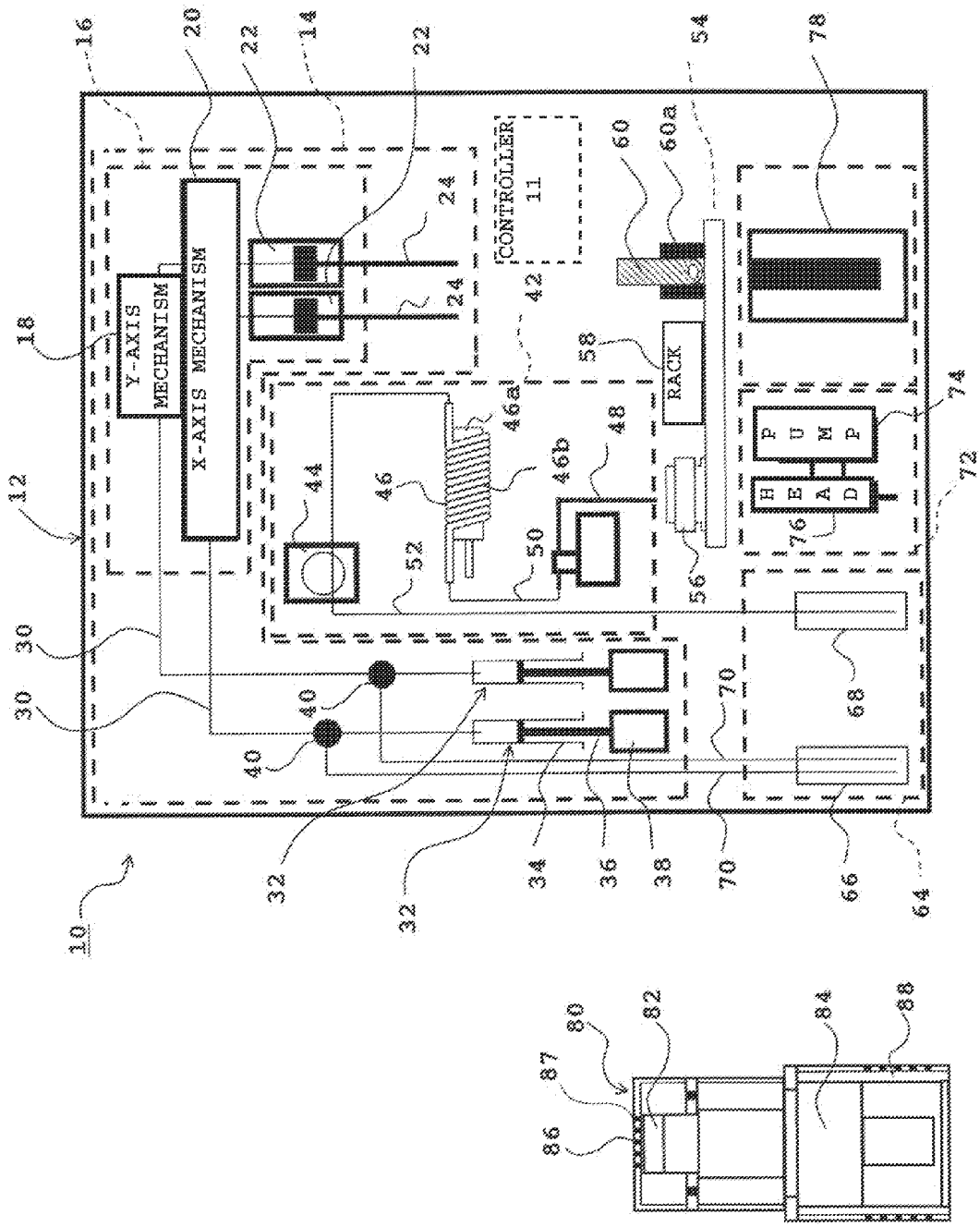
FIG. 1 is a block diagram that illustrates a configuration of a luminescence measurement apparatus.

First, an overall configuration of a luminescence measurement apparatus 10 to which a collection unit 80 of the present invention is applicable will be described with reference to FIG. 1. The luminescence measurement apparatus 10 to be described in the present embodiment is constituted of the collection unit 80 and a measurement unit 12.

Figure 2:
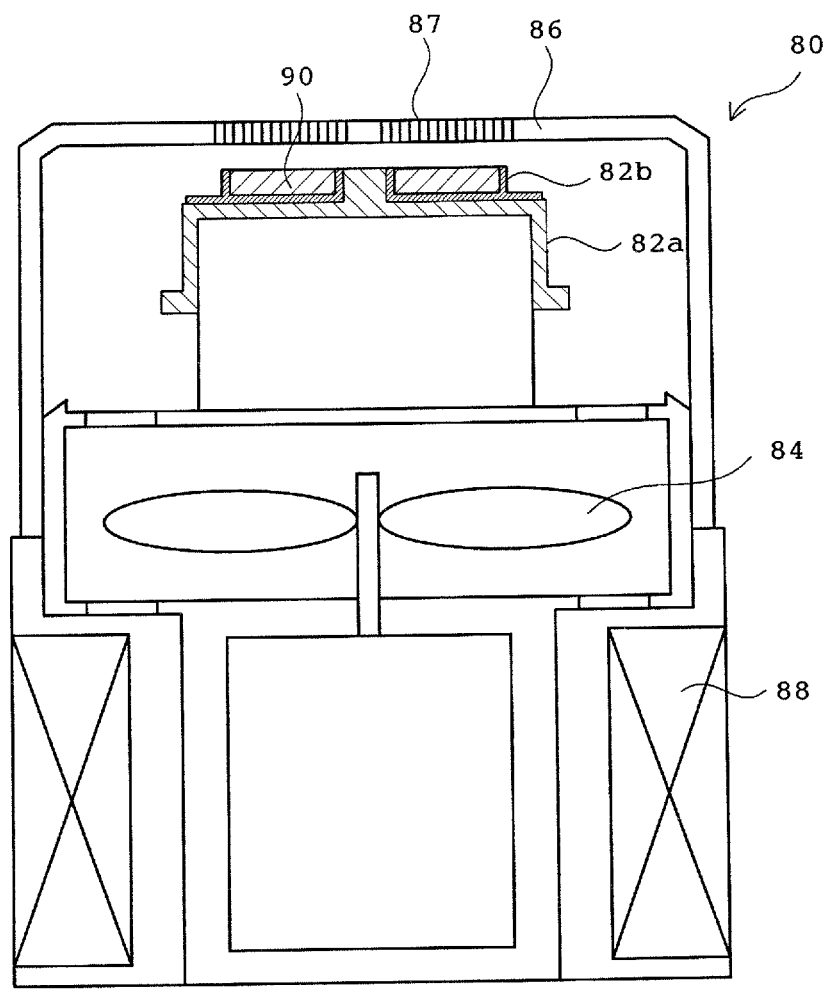
FIG. 2 is a block diagram that illustrates a detailed configuration of a collection unit.
Figure 3:
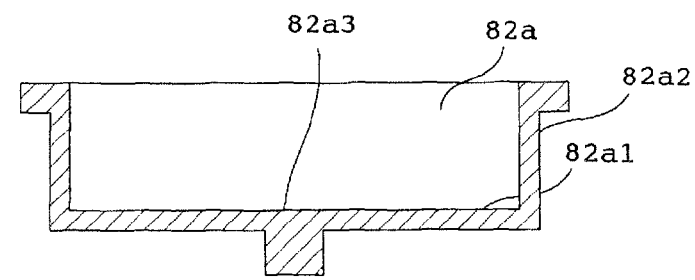
FIG. 3 is an exploded view that illustrates a configuration of a collection carrier cartridge.
Figure 3:
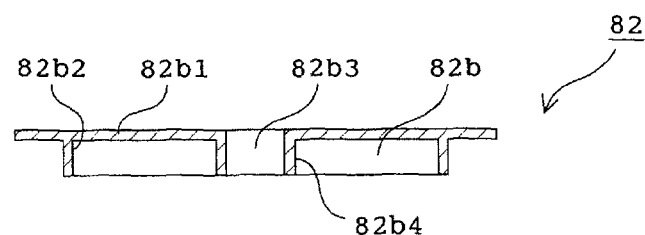
Figure 3:
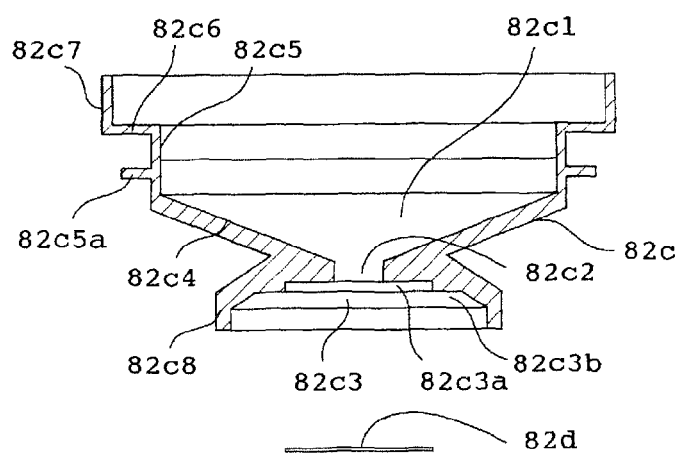
Figure 3:
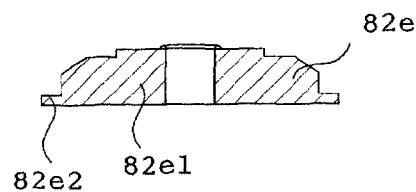
Figure 4A:
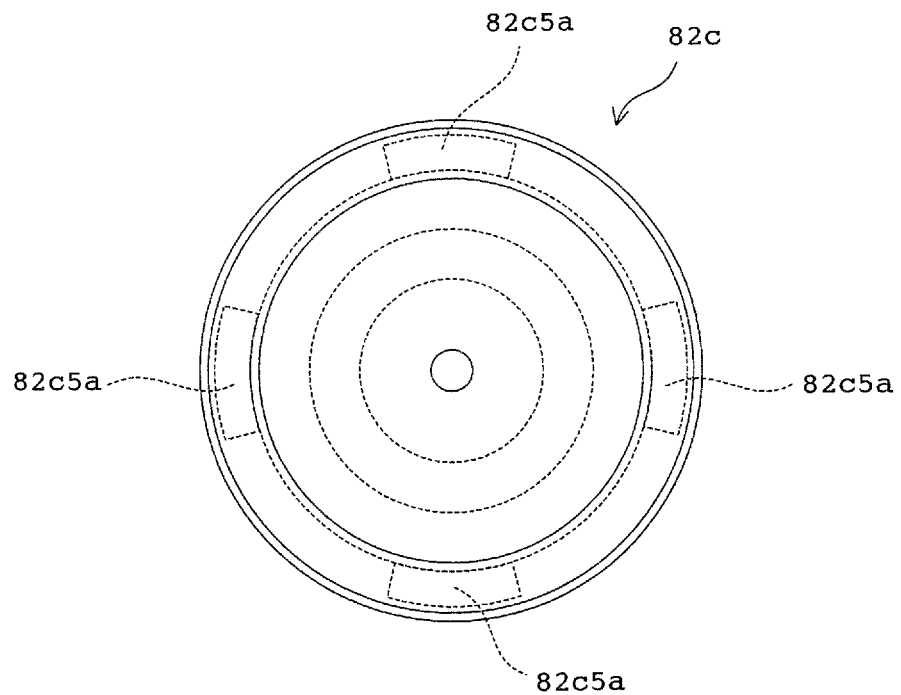
FIG. 4A is a plan view that illustrates a detailed configuration of a main body of the collection carrier cartridge.
Figure 4B:
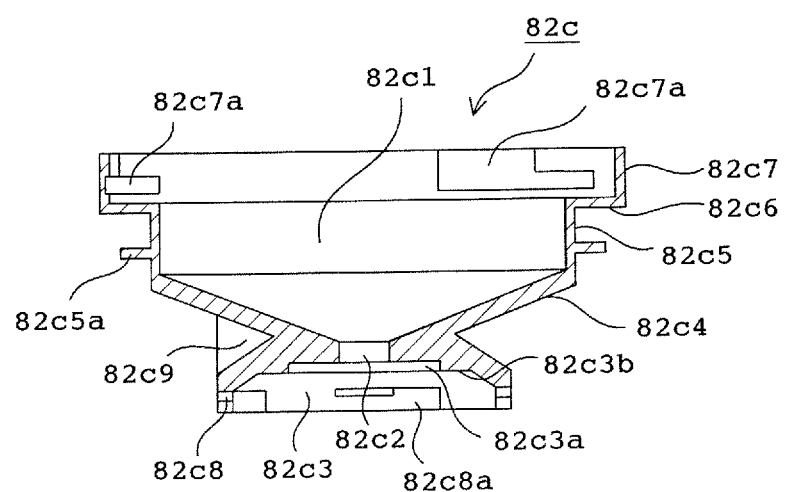
FIG. 4B is a cross-sectional view that illustrates a detailed configuration of the main body of the collection carrier cartridge.

As shown in FIG. 2, the collection unit 80 is a device for collecting viable bacteria in the air on a collection carrier 90 filled in a carrier filling dish 82b of a collection carrier cartridge 82 (see, FIG. 3). The collection unit 80 is mainly constituted of the carrier filling dish 82b of the collection carrier cartridge 82, an upper lid 82*a*, a blower fan 84, an impactor nozzle head 86, and an exhaust filer 88.

The collection carrier cartridge 82 having the carrier filling dish 82*b* plays a role of collecting viable bacteria floating in the air. As shown in FIG. 3, the collection carrier cartridge 82 according to the present embodiment is constituted of a main body 82*c*, the carrier filling dish 82*b*, the upper lid 82*a*, a filter 82*d*, and a filter fixing ring 82*e*.

The main body 82*c* is constituted of a storage portion 82*c*1, a filter placing portion 82*c*3, and a connection hole 82*c*2. As described in detail later, the storage portion 82*c*1 stores a solution prepared by diluting the molten collection carrier 90 with hot water. The inner surface of the storage portion 82*c*1 is constituted of a mortar-like inclined surface 82*c*4 inclining toward the connection hole 82*c*2 provided in the center, and this configuration allows the stored solution to flow into the connection hole 82*c*2 in the filtration. A first wall portion 82*c*5 formed vertically is provided on the upper end side of the mortar-like storage portion 82*c*1, and a second wall portion 82*c*7 is provided at the outer edge of the upper end of the first wall portion 82*c*5 through a flanged flat portion 82*c*6. The second wall portion 82*c*7 has an L-shaped groove 82*c*7*a* (see, FIG. 4B) provided on its inner wall, and this groove allows the upper lid 82*a* to be described in detail later to be connected in a bayonet manner. As to FIGS. 4A and 4B, FIG. 4A is a view that illustrates a planar configuration of a collection carrier cartridge body, and FIG. 4B is a view that illustrates a configuration of a front cross section of the collection carrier cartridge body.

The filter placing portion 82*c*3 is constituted of a concave groove portion 82*c*3*a* provided around the connection hole 82*c*2 and a mortar portion 82*c*3*b* provided around the concave groove portion 82*c*3*a*. The diameter of the mortar portion 82*c*3*b* is smaller than the diameter of the storage portion 82*c*1. A third wall portion 82*c*8 formed downward is provided at an end of the mortar portion 82*c*3*b*. The third wall portion 82*c*8 has on its inner wall an L-shaped groove 82*c*8*a* as in the second wall portion 82*c*7, and this groove allows the filter fixing ring 82*e* to be described in detail later to be connected in the bayonet manner.

The outer shape of the main body 82*c* of the collection carrier cartridge 82 having the above inner structure is constituted of: an outer wall formed into a drum shape along the inner wall of the storage portion 82*c*1 and the filter placing portion 82*c*3; a first outer wall portion provided along the first wall portion 82*c*5; an outer wall of the flat portion 82*c*6 connecting a second outer wall portion being an outer wall of the second wall portion 82*c*7 and the first outer wall portion; and a third outer wall portion being an outer wall of the third wall portion 82*c*8. A reinforcement portion 82*c*9 is formed between the outer wall of the storage portion 82*c*1 and the outer wall of the filter placing portion 82*c*3 along the range where the third outer wall portion is formed. Protrusions 82*c*5*a* used for fixing a main body to the cartridge holder as described above are provided on the outer circumference of the first wall portion 82*c*5. The protrusions 82*c*5*a* allow bayonet connection to a collection carrier cartridge holder (hereinafter referred to as a cartridge holder) 56 to be described in detail later.

The carrier filling dish 82*b* is constituted of a bottom plate 82*b*1, an inner bulkhead 82*b*4, and an outer bulkhead 82*b*2. The bottom plate 82*b*1 may be a flat plate having a diameter the same as or slightly smaller than the diameter of the second wall portion 82*c*7 of the main body 82*c* and has a small diameter through hole 82*b*3 in the center. The inner bulkhead 82*b*4 is a vertical wall provided along the through hole 82*b*3. The outer bulkhead 82*b*2 is a vertical wall provided as a circle having a diameter one size smaller than the diameter of the first wall portion 82*c*5 of the main body 82*c* and has a height the same as the height of the inner bulkhead 82*b*4. By employing such an arrangement form of the outer bulkhead 82*b*2, the outer edge portion of the bottom plate 82*b*1 has a flanged shape projecting outside the outer bulkhead 82*b*2. Thus, when the carrier filling dish 82b is set in the main body 82c so that the inner bulkhead 82b4 and the outer bulkhead 82b2 face the storage portion 82c1, the outer bulkhead 82b2 is fitted inside the first wall portion 82c5, and the outer edge of the bottom plate 82b1 is caught on the flat portion 82c6, so that the position of the carrier filling dish 82b is placed (the connection state is shown in FIG. 12B). The through hole 82b3 and the connection hole 82c2 are arranged linearly, so that a hot-water supply nozzle 48 or a reagent dispensing nozzle 24 can fall above a filter 82d placed in a filter placing portion 82c3 through the inside of the through hole 82b3.

The upper lid 82a has a base 82a1 and a frame portion 82a2 and is a member used for setting the carrier filling dish 82b in the collection unit 80. The base 82a1 is a placing stage for placing the carrier filling dish 82b. The base 82a1 is a circle having a diameter slightly larger than the diameter of the bottom plate 82b1 in the carrier filling dish 82b and slightly smaller than the diameter of the second wall portion 82c7 of the main body and has a protrusion 82a3 of the center. The protrusion 82a3 has a columnar shape, and the diameter corresponds to the diameter of the through hole 82b3 provided in the carrier filling dish 82b. With this configuration, the carrier filling dish 82b can be placed in such a state that the protrusion 82a3 is inserted through the through hole 82b3. Consequently, it is possible to prevent the carrier filling dish 82b from being displaced on the base 82a1 by the airflow substantially vertically coming into contact with the luminescence measurement apparatus 10 when the blower fan 84 is activated. The frame portion 82a2 is a wall portion provided at an outer edge of the base 82a1 and provided upright toward the opposite side of a surface on which the carrier filling dish 82b is placed. A plurality of protrusions (not shown) are provided on the outer circumference of the frame portion 82a2 and form a bayonet connection mechanism with the second wall portion 82c7.

The filter fixing ring 82e is a member used for fixing the filter 82d placed in the concave groove portion 82c3a of the main body 82c and is constituted of: a protrusion 82e1 formed corresponding to the shapes of the concave groove portion 82c3a and the mortar portion 82c3b and the height of the third wall portion 82c8; and a flange portion 82e2 formed at the lower end outer circumference of the protrusion 82e1. The filter fixing ring 82e also has on the outer circumference of the protrusion 82e1 a protrusion (not shown) corresponding to an L-shaped groove 82c8a provided in the third wall portion 82c8, and the protrusion forms a bayonet connection mechanism with the filter placing portion 82c3.

The collection carrier 90 for collecting viable bacteria is provided in the carrier filling dish 82b of the collection carrier cartridge 82. The collection carrier 90 used in the present embodiment is in a gel state at the time of collection (at normal temperature) and solates when heated to 40° C. or lower. Especially, it is preferable to use a collection carrier having a phase transition temperature of 15° C. to 37° C., being in a gel state with a suitable strength at 25° C., and solating in a few minutes at 37° C. When the collection carrier is phase-transited within that temperature range, collected viable bacteria can be took out without being killed. As an example of the collection carrier 90, a collection carrier containing gelatin or NAGAm/MBPDA is preferably used. Thus, the heated collection carrier 90 solates to be stored in the storage portion 82c1 of the main body 82c, and diluted with hot water for dilution supplied from the hot-water supply section 42.

The blower fan 84 has a role of suctioning air into the collection unit 80 and impacting floating bacteria in the air against the collection carrier 90 in the carrier filling dish 82b described above. In order to prevent detection error due to contamination of the blower fan 84 itself, the blower fan 84 is preferably arranged on a downstream side from the position where the carrier filling dish 82b is arranged (on a lower side in the collection unit 80 because the suction port is located in an upper portion according to the present embodiment). In the collection unit 80, an amount of the air to be collected can be determined based on a blow amount and operation time of the blower fan 84.

The impactor nozzle head 86 is placed in an upper portion of the collection unit 80 and has a role of a cover for the carrier filling dish 82b and an accelerator. A velocity of the air inflowing to the collection unit 80 is required high to some extent for impacting viable bacteria against the collection carrier 90 of the carrier filling dish 82b and supporting by the collection carrier 90. However, in order to obtain high velocity, there is a concern about size increase of the collection unit 80 because a size of the blower fan 84 as a movable portion and the rotation rate of the blower fan 84 are required to increase.

Figure 5:
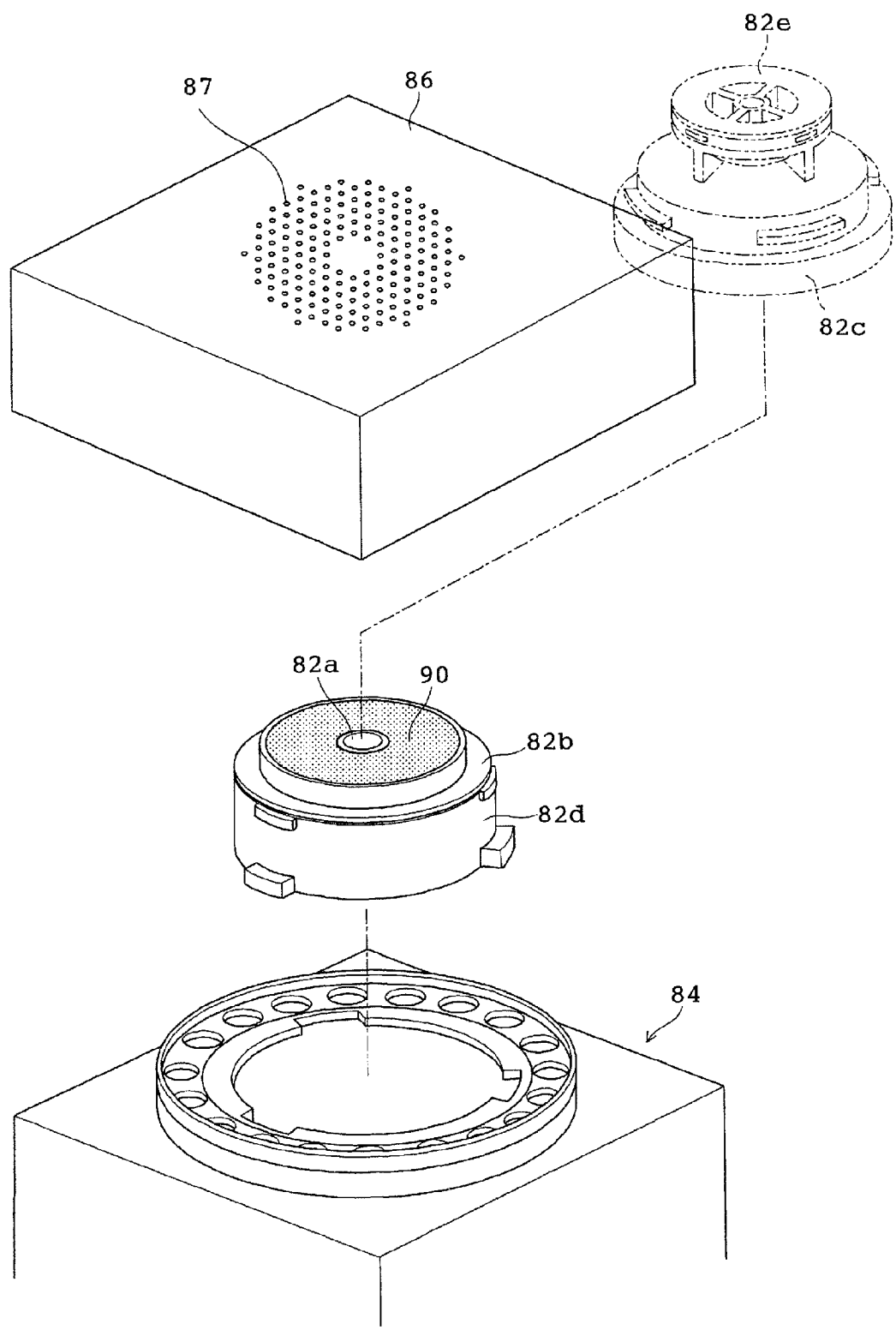
FIG. 5 is an exploded perspective view of an impactor nozzle head and the collection carrier cartridge constituting the collection unit.
Figure 6:
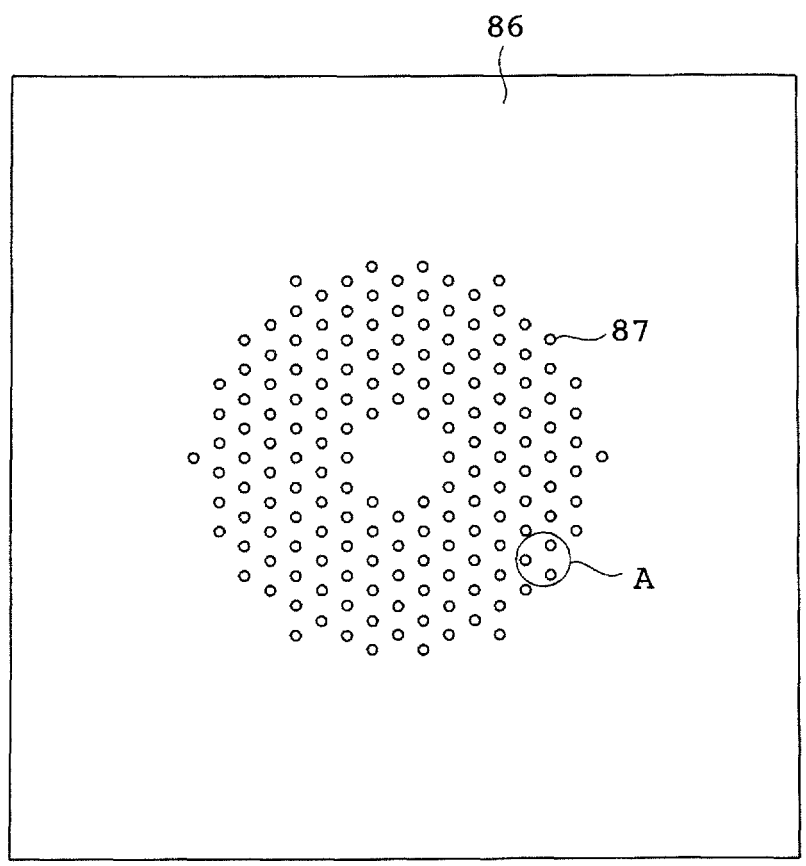
FIG. 6 is a plan view of the impactor nozzle head.
Figure 7:
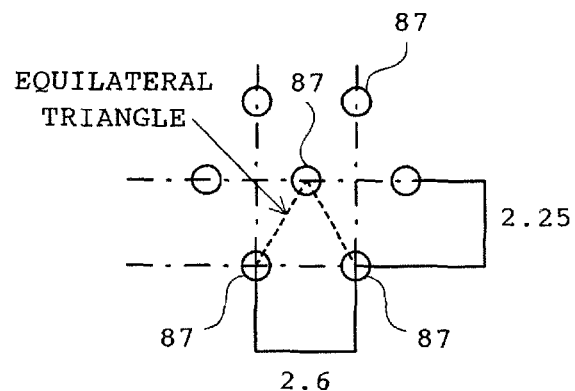
FIG. 7 is a partial enlarged view of an A portion of FIG. 6.
Figure 8:
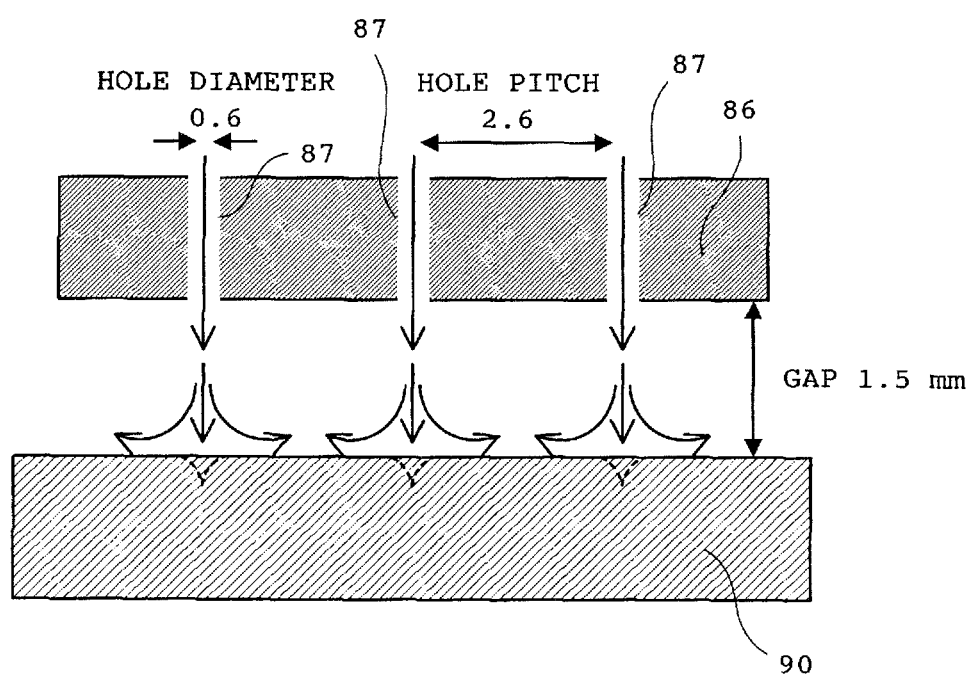
FIG. 8 is an explanatory view of a nozzle hole.

FIG. 5 is an exploded perspective view of the impactor nozzle head and the collection carrier cartridge constituting the collection unit. FIG. 6 is a plan view of the impactor nozzle head. FIG. 7 is a partial enlarged view of a portion A of FIG. 6. FIG. 8 is an explanatory view of a nozzle hole. In the impactor nozzle head 86, a plurality of small-diameter nozzle holes 87 are provided, so that the air suctioned by the blower fan 84 passes through the nozzle holes 87 and is impacted against the collection carrier 90. In a case of constant air flow, a velocity of passing fluid can be increased by narrowing an area of a flow passage through which the fluid passes. Thus, necessary velocity can be obtained without increasing the size and the rotation rate of the blower fan 84.

As shown in FIG. 6, the impactor nozzle head 86 has a plurality of nozzle holes 87. No nozzle hole 87 is not formed in a position being the center of the impactor nozzle head 86 and facing the protrusion 82a3 of the upper lid 82a and the through hole 82b3 of the carrier filling dish 82b. The nozzle holes 87 can be alternately arranged in a zigzag pattern so that the adjacent holes are arranged in two rows at predetermined intervals. As an example, the nozzle holes 87 of the present embodiment are arranged in such a manner that the centers of the adjacent nozzle holes are arranged at the respective apexes of an equilateral triangle in plan view of the circular impactor nozzle head 86 as shown in FIG. 7. With this configuration, air can be uniformly impacted against the collection carrier 90 facing the nozzle holes 87. In addition to this configuration, the nozzle holes 87 may be arranged in a zigzag pattern in such a manner that the centers of the nozzle holes are arranged at the apexes of an isosceles right triangle, so that air is uniformly impinged against the collection carrier 90.

As to the pitch between the nozzle holes 87, the length of one side of the equilateral triangle (distance between the hole centers) is set to 2.6 mm. The hole diameter of the nozzle holes 87 is set to 0.6 mm. A clearance between the impactor nozzle head 86 and the collection carrier 90 is set to 1.5 mm. With this configuration, the velocity of air passing through the nozzle holes 87 can be set to 40 to 50 m/s.

The exhaust filter 88 is placed on the downstream side of the blower fan 84 (on the lower side in the collection unit 80 according to the present embodiment) and has a role of removing dust contained in the exhaust. As an example of the exhaust filter 88, a cylindrical ULPA filter (Ultra Low Penetration Air Filter) covering an outer circumference of a fan drive motor may be used.

With the above configuration, in the collection unit 80 according to the present embodiment, while the velocity of the air passing through the nozzle holes is maintained at a predetermined value, the size of the fan is not increased and thus the entire unit can be reduced in weight and size.

The measurement unit 12 has a reagent dispensing section 14, a hot-water supply section 42, a reagent/carrier container mounting section 54, a buffer supply section 64, a filtration section 72, a PMT (Photomultiplier tube) section 78, and an input/control section (hereinafter referred to as a controller) 11. Such the respective component elements are arranged in an outer shell.

Figure 9:
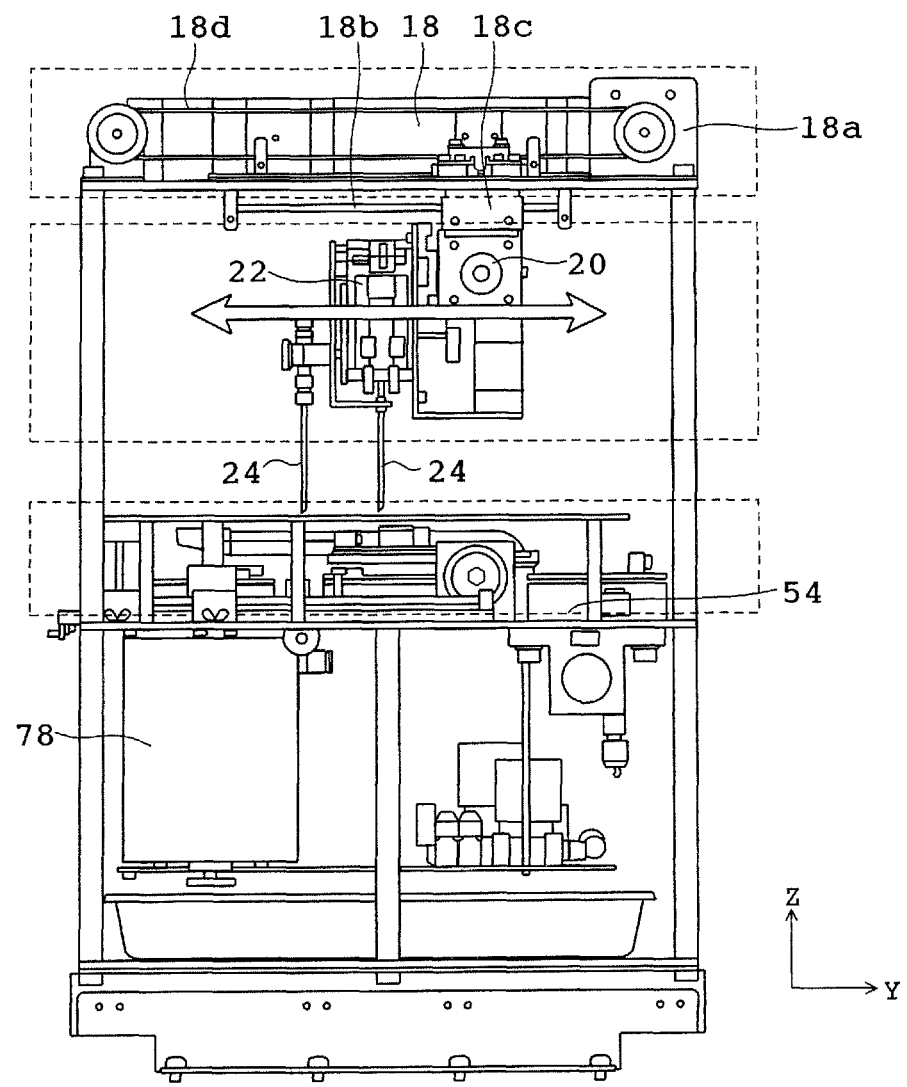
FIG. 9 is a schematic view that illustrates a side configuration of a measurement unit.

The reagent dispensing section 14 is mainly constituted of a triaxial actuator 16, the reagent dispensing nozzle 24, and a syringe pump 32. The triaxial actuator 16 is means for moving the reagent dispensing nozzle 24 to be described in detail later to a desired position. Thus, as illustrated in detail in FIG. 9, the triaxial actuator 16 is constituted of a Y-axis mechanism portion 18, an X-axis mechanism portion 20, and a Z-axis mechanism portion 22. If the Y-axis mechanism portion 18 can be arranged at an upper portion of the apparatus, space is not restricted so much. Thus, in the measurement unit 12 in the present embodiment, a stepping motor 18a is used as a driving actuator, and an operation portion 18c attached to a linear guide 18b is slid by a driving belt 18d.

On the other hand, it is difficult to allow enough space for the X-axis mechanism portion 20 and the Z-axis mechanism portion 22 attached to the operation portion 18c. Thus, compact actuators are employed for both the X-axis mechanism portion 20 and the Z-axis mechanism portion 22. A compact actuator is a small-size actuator obtained by integrating a motor and a projecting shaft by incorporating a large-diameter thrust shaft system into a hollow rotor. As an operation principle, a stepping motor is used as a driving system and a ball screw is used as the projecting shaft. Accordingly, the mechanism portions of such a compact size enable highly accurate positioning.

Figure 10A:
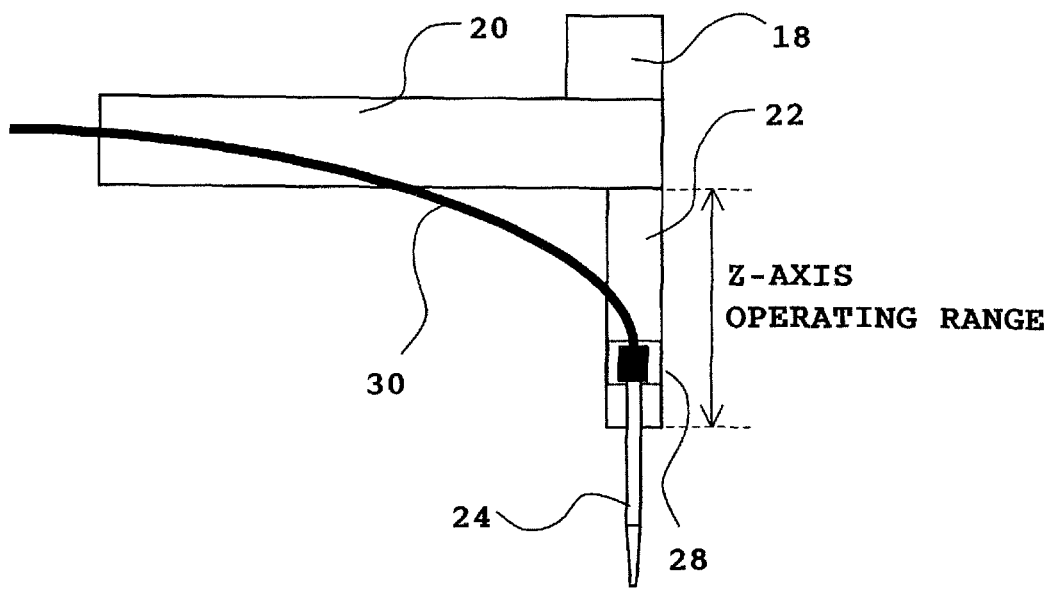
FIG. 10A is a front block diagram that illustrates a configuration of a reagent dispensing nozzle.
Figure 10B:
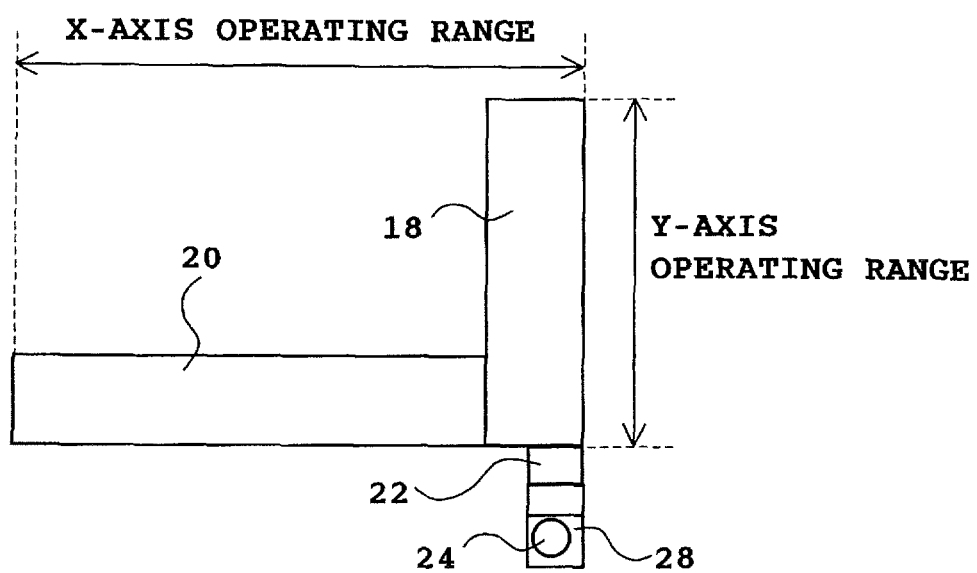
FIG. 10B is a plan block diagram that illustrates a configuration of the reagent dispensing nozzle.
Figure 11:
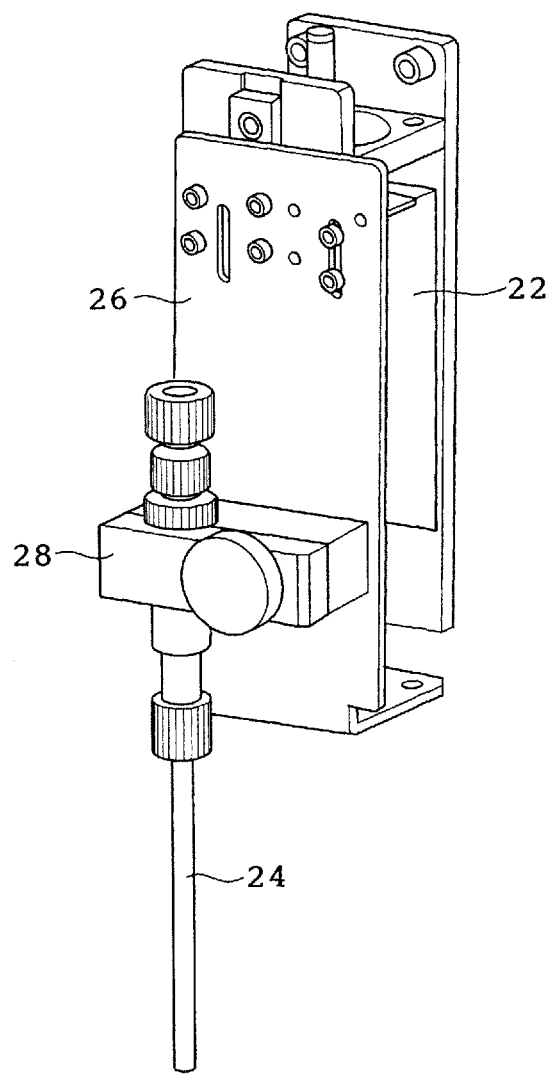
FIG. 11 is a reference perspective view that illustrates a relationship between a Z-axis mechanism portion, a fixation block, and the reagent dispensing nozzle.

The reagent dispensing nozzle 24 is a nozzle which plays a role of dividing and dispensing desired amounts of various reagents used for luminescence measurement. As shown in FIGS. 10 and 11, the reagent dispensing nozzle 24 is supported by a fixation block 28 equipped in a slide guide 26 attached to the compact actuator as the Z-axis mechanism portion 22. Such the supporting configuration facilitates stabilization of an up-and-down operation. As to FIGS. 10A and 10B, FIG. 10A is a front block diagram showing a relationship between schematic configuration of the triaxial actuator 16 and the reagent dispensing nozzle 24. FIG. 10B is a block diagram showing a top configuration in FIG. 10A. FIG. 11 is a reference perspective view showing a relationship between the Z-axis mechanism portion 22 and the reagent dispensing nozzle 24.

A dispensing operation pipe 30 connected to the syringe pump 32 to be described in detail later is connected to a back end of the reagent dispensing nozzle 24. The reagent dispensing nozzle 24 divides a reagent by applying negative pressure in the nozzle through the dispensing operation pipe 30 and dispenses thus divided reagent by applying positive pressure in the nozzle. The reagent dispensing nozzle 24 may be formed by a resin-made pipe or a metal-made pipe as well as a glass-made pipe.

The syringe pump 32 plays a role of controlling an actuation fluid (pure water in the present embodiment) for dividing and dispensing a reagent through the reagent dispensing nozzle 24. The syringe pump 32 is mainly constituted of a syringe 34, a plunger 36, and an actuator 38. The syringe 34 is a tank for storing pure water being an actuation fluid. The plunger 36 is a push stick which plays a role of introducing pure water into the syringe 34 and discharging pure water by applying negative pressure or positive pressure in the syringe 34. The actuator 38 is driving means for plunging or extracting the plunger 36. It is possible to accurately control positioning by using a stepping motor and a ball screw or the like for the actuator 38.

One end of the dispensing operation pipe 30 is connected to a tip end of the syringe 34 in the syringe pump 32 having the above configuration, and other end of the dispensing operation pipe 30 is connected to the reagent dispensing nozzle 24 described above. With the dispensing operation pipe 30 connected in this way, pure water is stored in the syringe 34 and negative pressure is applied in the nozzle of the reagent dispensing nozzle 24, and a reagent is injected (divided) into the reagent dispensing nozzle 24 when the plunger 36 is extracted. On the contrary, when the plunger 36 is plunged, pure water discharged from the syringe 34 is moved to the reagent dispensing nozzle 24, and thus a pressure inside the reagent dispensing nozzle 24 increases, and the reagent stored inside the reagent dispensing nozzle 24 is ejected (dispensed).

A buffer supply pipe 70 connected to a buffer supply section 64 to be described in detail later is connected to the dispensing operation pipe 30 through a distribution valve 40 such as three-way valve. With this configuration, pure water as an operation fluid stored inside the dispensing operation pipe 30 can be periodically changed. Consequently, error of measurement data due to contamination of the operation fluid can be prevented.

The hot-water supply section 42 plays a role of supplying hot water for diluting the collection carrier 90. The hot-water supply section 42 is mainly constituted of a peristaltic pump 44, a heater 46, and a hot-water supply nozzle 48. The peristaltic pump 44 is mainly constituted of a resin tube, a roller, and an actuator (none of them shown in the figure). The resin tube is a tube used for sending solution, and transportation fluid (pure water in the present embodiment) flows therein. The tube preferably has flexibility and durability because the tube is mechanically compressed by the roller, and, for example, silicon tube is preferable. The roller plays a role of repeating rotation and revolution while compressing the resin tube to push out the transportation fluid, which is confined in a compression region, in a direction of roller revolution. Force of reverting to the original form is applied on the resin tube thus compressed by the roller. Since the transportation fluid is an incompressible fluid, revolution of plural rollers continuously push out the transportation fluid. Here, the actuator may be one capable of making plural rollers rotate.

With the peristaltic pump 44 having the above configuration, the pump itself is not contaminated since a contact portion with the transportation fluid (pure water in the present embodiment) is only inside the tube through which the transportation fluid flows. Thus, it is easy to maintain an aseptic condition and clean.

The heater 46 plays a role of heating the pure water as a transportation fluid. Although the configuration of the heater 46 is not limited particularly, a cartridge heater and a tube heater are preferably employed when compactness is emphasized. For example, when the cartridge heater is employed, a pipe made of metal (hereinafter referred to as a metal pipe 46b) is wound around a heater body 46a, and the pure water as a transportation fluid may be sent through the metal pipe 46b thus wound. Because with such configuration, the pure water inside the metal pipe 46b is heated by heat transfer. Meanwhile, when a tube heater is employed, a rubber heater is wound around the resin pipe (tube) and so on, and the pure water as a transportation fluid sent through the resin tube is heated. With this configuration, a heat transfer rate can be excellent by employing a silicon resin and so on for the resin tube. Since both of the resin tube and the rubber heater are flexible, piping can be highly flexible, and thus a heat region can be secured to be long. Thus, it is possible to avoid temperature decrease after being heated, in other word, facilitate temperature stabilization. Although arrangement position of the heater 46 is not limited particularly, a fluid transportation distance after being heated is preferably short in order to avoid temperature decrease after being heated. Thus, in the measurement unit 12 according to the present embodiment, the heater 46 is arranged between the above-described peristaltic pump 44 and the hot-water supply nozzle 48 to be described in detail later.

The hot-water supply nozzle 48 is an ejection nozzle for supplying hot water (pure water) which is transferred by the peristaltic pump 44 and heated by the heater 46 to the main body 82c of the collection carrier cartridge 82 which is arranged in the reagent/carrier container mounting section 54 to be described in detail later. It may be configured by a metal (SUS) pipe and so on or may be a glass pipe and a resin pipe as well. A hot water supply pipe 50 connected to the peristaltic pump 44 through the heater 46 is connected to an end on the opposite side of the ejection port in the hot-water supply nozzle 48. A suction side pipe 52 in the peristaltic pump 44 is connected to the buffer supply section 64 to be described in detail later.

With the hot-water supply section 42 having the above configuration, hot water can be continuously ejected from the hot-water supply nozzle 48 by driving the peristaltic pump 44.

The reagent/carrier container mounting section 54 is a stage for arranging a reagent used for the luminescence measurement and a collection carrier. A cartridge holder 56, a reagent rack 58, a luminescence measurement tube holder 60a, and so on are arranged in the reagent/carrier container mounting section 54. The cartridge holder 56 is a holder on which the main body 82c, the carrier filling dish 82b, the filter 82d, and the filter fixing ring 82e in the collection carrier cartridge 82 are set. The cartridge holder 56 having a built-in heater so that thus set collection carrier cartridge 82 can be heated.

Figure 12A:
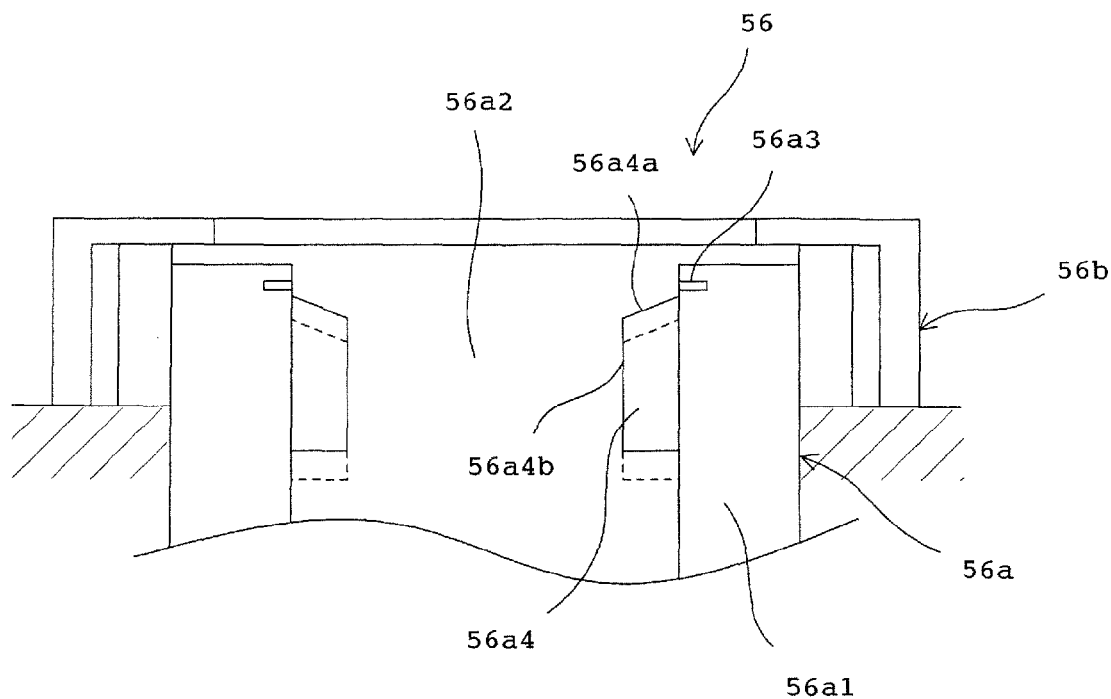
FIG. 12A is a cross-sectional block diagram that illustrates a configuration of a collection carrier cartridge holder.
Figure 12B:
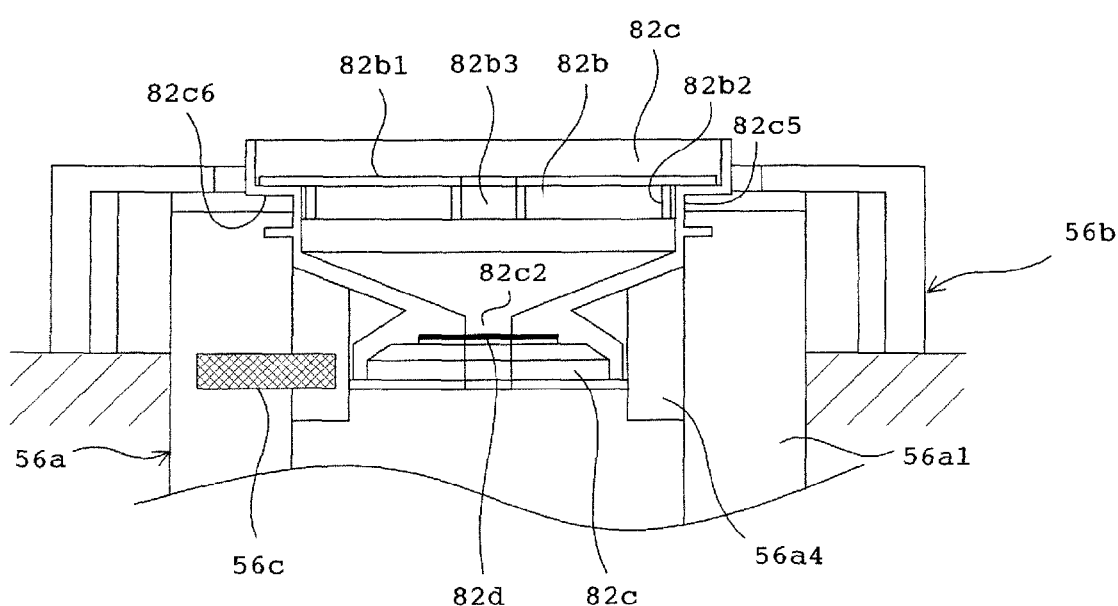
FIG. 12B is a cross-sectional block diagram that illustrates a configuration in which the cartridge body is connected to the collection carrier cartridge holder.

As shown in FIGS. 12A and 12B, the cartridge holder according to the present embodiment is constituted of a holder main body 56a and a heat insulation case 56b. As to FIGS. 12A and 12B, FIG. 12A is a view that illustrates a cross-sectional configuration of the cartridge holder, and FIG. 12B is a cross-sectional configuration view that illustrates a state that a main body of the collection carrier cartridge is assembled onto the cartridge holder.

The holder main body 56a is constituted of: an opening 56a2 in which a suction head 76 in the filtration section 72 to be described in detail later; and a holder portion provided on the outer circumference of the opening 56a2. The holder portion is constituted of a movable block 56a4 and a fixation block 56a1. The movable block 56a4 has a contact surface constituted of an inclined surface 56a4a along the outer wall of the storage portion 82c1 of the collection carrier cartridge 82 and a vertical surface 56a4b provided upright at lower and upper ends of the inclined surface 56a4a.

The movable block 56a4 is a holding mechanism placed inside the fixation block 56a1. The fixation block 56a1 has in its inner wall surface a groove 56a3 in which the protrusions 82c5a provided in the main body 82c of the collection carrier cartridge 82 as described above are fitted. The movable block 56a4 supports the main body 82c set in the holder main body 56a and, at the same time, pushes the main body 82c upward, whereby the holder main body 56a can hold the main body 82c stably.

The holder main body 56a is formed of a material with a high heat transfer efficiency, such as aluminum, and a cartridge heater (heater) 56c inserted (buried) in the holder main body 56a heats the collection carrier cartridge 82 through the holder main body 56a (and a contact surface with the collection carrier cartridge 82). As the heater 56, any heater may be used as long as it can heat the collection carrier cartridge 82 set in the holder main body 56a to a predetermined temperature, and, for example, a rubber heater covering the holder main body 56a in the form of a ring or a cap may be used. The heat insulation case 56b is a cover which covers the outer peripheral surface and the upper surface of the holder main body 56a so that the holder main body 56a, which is a heating element, is not directly exposed to the outside. Although the material of the heat insulation case 56b is not particularly limited, it is preferable that the heat insulation case is formed of a material having low heat conductivity, for example, a heat resistant resin or the like. According to this configuration, the (cartridge) heater 56c can heat the main body 82c of the collection carrier cartridge 82 through the holder main body 56a by the action of heat transfer and heat conduction.

Figure 13A:
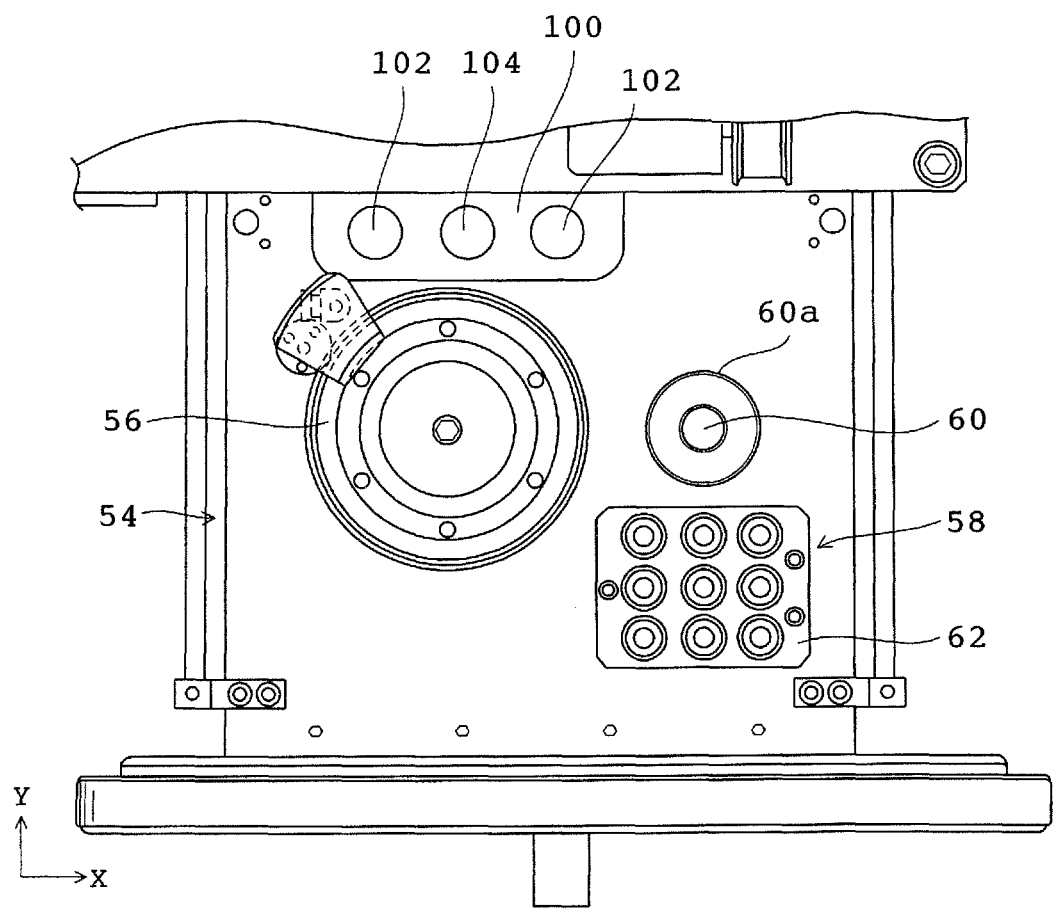
FIG. 13A is a top view that illustrates a configuration of a reagent/carrier container mounting section.
Figure 13B:
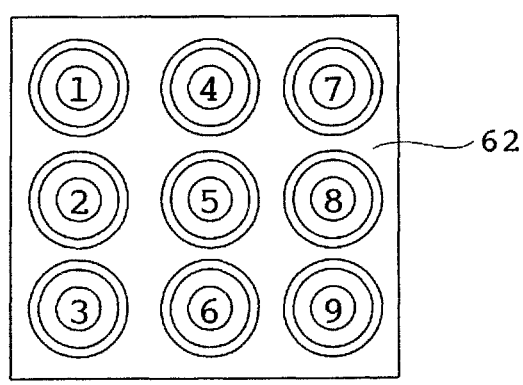
FIG. 13B is a top view that illustrates a configuration of a reagent cartridge of the reagent/carrier container mounting section.

The reagent cartridge filled with a reagent used for the luminescence measurement is placed in the reagent rack 58. As shown in FIGS. 13A and 13B, the reagent cartridge is a package where various types of reagents, pure water, and so on are filled in respective recesses which are separated (nine in an example shown in FIG. 13B), and an upper opening of the recesses are sealed with an aluminum sheet (film) and so on. According to this configuration, the reagents are not exposed to outside until the aluminum sheet is removed and opens, and the stocked reagents are not contaminated by viable bacteria and so on. As to FIGS. 13A and 13B, FIG. 13A is a top view of the reagent/carrier container mounting section 54, and FIG. 13B is a top view of the reagent cartridge 62.

A luminescence measurement tube 60 is placed in the luminescence measurement tube holder 60a. The luminescence measurement tube 60 is a micro tube for conducting a luminescence reaction of ATP which is extracted from viable bacteria collected on the filter 82d in the collection carrier cartridge 82.

The buffer supply section 64 has a reagent dispensing nozzle control water tank (hereafter referred to as a control water tank 66) and a hot-water supply water tank 68. Since a process of removing free ATP is not included in a process after the reagent dispensing nozzle 24 is used, a cleanliness level of the water (pure water) in the control water tank 66 filled in the dispensing operation pipe 30 which connects the syringe pump 32 and the reagent dispensing nozzle 24 is required to be kept higher than the cleanliness level of the water (pure water) in the hot-water supply water tank 68. Thus, volume of the control water tank 66 is smaller than that of the hot-water supply water tank 68 and stored water is appropriately exchanged. Water in the hot-water supply water tank 68 requires larger volume than that of the control water tank 66 because the water is poured in the storage portion 82c1 in the main body 82c of the collection carrier cartridge 82 set in the collection carrier cartridge holder 56.

The control water tank 66 set as described above is connected to the distribution valve 40 in the dispensing operation pipe 30 through the buffer supply pipe 70 so that pure water can be supplied to the dispensing operation pipe 30 by switching the distribution valve 40. The hot-water supply water tank 68 is connected to a suction side of the peristaltic pump 44 described above and suctioned by driving the peristaltic pump 44.

The filtration section 72 plays a role of removing the collection carrier 90 (collection carrier solution) in the storage portion 82c1 which is diluted by hot water ejected from the hot-water supply nozzle 48. The filtration section 72 is mainly constituted of a suction pump 74 and a suction head 76. The suction pump 74 is a pump for producing negative pressure inside the suction head 76 to be described in detail later. Further, the suction head 76 is an open-end cylindrical body. The end of the suction head 76 contacts with a lower surface flat portion of the filter fixing ring 82e in the collection carrier cartridge 82. Thus, an O ring 76a is placed at the end of the suction head 76 so that leakage of air during the suction of air can be prevented.

The suction head 76 is provided with an actuator (not shown) which plays a role of pressing the end of the suction head 76 against the lower end portion of the main body 82c of the capturing carrier cartridge 82 assembled onto the cartridge holder 56, that is, the lower surface of the filter fixing ring 82e with a predetermined pressure based on the control signal sent from a controller 11. According to this configuration, a state that a predetermined pressure is applied to the lower surface of the main body 82c fixed to the cartridge holder 56 is maintained during the suction of air.

In the filtration section 72 having the above basic configuration, an end thereof is connected to a lower portion of the collection carrier cartridge holder 56, and then the suction pump 74 is operated, whereby the collection carrier diluted by hot water can be suctioned and removed trough the filter 82d.

The PMT section 78 plays a role of measuring luminescence amount of the ATP in the luminescence measurement tube 60. In the measurement unit 12 according to the present embodiment, the PMT section 78 is a head-on type and arranged at a lower portion of the luminescence measurement tube 60 described above. According to this configuration, light produced in the luminescence measurement tube 60 enters from the upper portion of the PMT section 78, and the luminescence amount is measured.

The controller 11 is a component element which controls the component elements described above with respect to an input value to the luminescence measurement apparatus 10 and thereby automates luminescence measurement.

Figure 14:
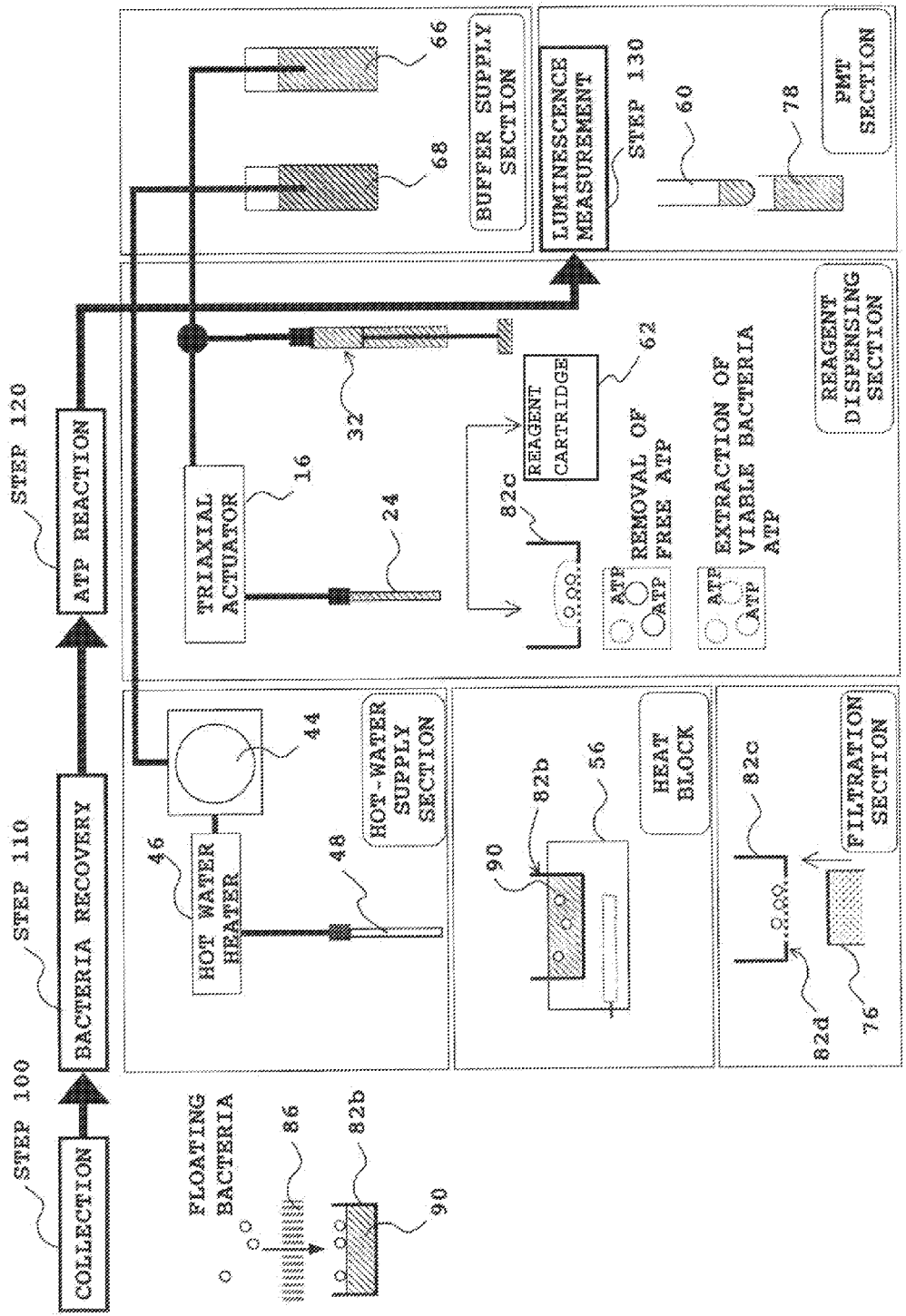
FIG. 14 is a flow diagram for explaining each operation process in a reagent dividing/dispensing mechanism.

When the luminescence measurement apparatus 10 constituted of the collection unit 80 having the above basic configuration and the measurement unit 12 is used, the collection unit 80 is installed in a collection place and activated first, and airborne bacteria in the collection plate are suctioned to be collected on the collection unit 80 (step 100: see, FIG. 14).

In the collection process performed by the collection unit 80, specifically, the blower fan 84 is operated to suction air outside the collection unit 80 through the nozzle holes 87 zigzag-arranged on the upper surface of the impactor nozzle head 86, and then, to discharge the air to the outside of the collection unit 80 via the exhaust filer 88 and an outlet. The velocity of air passing through the nozzle holes 87 is 40 m/s to 50 m/s. Floating bacteria in the air are carried by an airflow substantially vertically coming into contact with the collection unit 80 through the nozzle holes 87 as shown in FIG. 8 to be impacted against the gelled collection carrier 90 by inertia and then to be collected by the collection carrier 90. Fine particles with a particle diameter smaller than air and bacteria that has been impacted against the collection carrier 90 change their direction to a direction parallel to the surface of the collection carrier 90, and thus, they are carried to a gap, the blower fan 84, and then to the exhaust filer 88. Since the fine particles with a particle diameter smaller than bacteria are captured by the exhaust filer 88, clean air not containing the fine particles is discharged outside the collection unit 80 through the exhaust filer 88 and the outlet.

Next, the carrier filling dish 82b in the collection carrier cartridge 82 in which viable bacteria are collected is removed from the collection unit 80 and assembled onto the cartridge holder 56 of the measurement unit 12 in such a state that the carrier filling dish 82b is set in the main body 82c. The main body 82c set in the cartridge holder 56 is heated by the heater 56c. The collection carrier solates by heating. The collection carrier 90 in sol form is stored in the storage portion 82c1 of the main body 82c and, diluted by hot water supplied from the hot-water supply nozzle 48 inserted in the through hole 82b3 of the carrier filling dish 82b. The diluted collection carrier 90 (collection carrier solution) is suctioned and removed by the filtration section 72 through the filter 82d so that viable bacteria and free ATP collected by the collection carrier 90 remain on the filter 82d. In the filtration section 72, the controller 11 outputs a control signal to an actuator (not shown) of the suction head 76. The actuator that has received the control signal presses the suction head 76 against the filter fixing ring 82e at the lower portion of the main body 82c with a predetermined pressure to eliminate a gap formed between the main body 82c and the filter fixing ring 82e. While the actuator (not shown) maintains this state, the controller 11 outputs an operation signal to the suction pump 74 of a suction portion, and the suction operation of the collection carrier solution is performed (step 110: see, FIG. 14).

After filtering the collection carrier 90, the reagent dispensing section 14 is operated for removing free ATP, extracting ATP from viable bacteria, and dividing a sample. First, a reagent is divided from the reagent cartridge 62 by the reagent dispensing nozzle 24 inserted into the through hole 82b3 of the carrier filling dish 82b and dispensed into the collection carrier cartridge 82, and free ATP is removed. With this operation, it is possible to prevent error in measuring a luminescence amount due to a luminescence reaction caused by the free ATP. Next, an ATP extraction reagent is dispensed on the filter 82d in the collection carrier cartridge 82 from which of the free ATP is removed so as to extract ATP derived from viable bacteria (step 120: see, FIG. 14).

After the extraction of the ATP derived from viable bacteria, luminescence reagent is dispensed in the luminescence measurement tube 60. Then, the ATP derived from viable bacteria is divided from the filter 82d and dispensed in the luminescence measurement tube 60 in which the luminescence reagent is dispensed, and the luminescence strength is measured by the PMT section 78 (step 130: see, FIG. 14).

With the collection unit according to the above embodiment, even in such a structure that the size of the entire unit is reduced, air passing through nozzle holes of an impactor nozzle head can be maintained at a predetermined velocity, and the floating bacteria collecting performance can be enhanced.

REFERENCE SIGNS LIST

10 . . . Luminescence measurement apparatus, 11 . . . Input/control section (controller), 12 . . . Measurement unit, 14 . . . Reagent dispensing section, 16 . . . Triaxial actuator, 18 . . . Y-axis mechanism portion, 20 . . . X-axis mechanism portion, 32 . . . Z-axis mechanism portion, 24 . . . Reagent dispensing nozzle, 26 . . . Slide guide, 28 . . . Fixation block, 30 . . . Dispensing operation pipe, 32 . . . Syringe pump, 34 . . . Syringe, 36 . . . Plunger, 38 . . . Actuator, 40 . . . Distribution valve, 42 . . . Hot-water supply section, 44 . . . Peristaltic pump, 46 . . . Heater, 48 . . . Hot-water supply nozzle, 50 . . . Hot water supply pipe, 52 . . . Suction side pipe, 54 . . . Reagent/carrier container mounting section, 56 . . . Collection carrier cartridge holder (cartridge holder), 56*a* . . . Holder body, 56*b* . . . Heat insulation case, 56*c* . . . Cartridge heater (heater), 58 . . . Reagent rack, 60 . . . Luminescence measurement tube, 60*a* . . . Luminescence measurement tube holder, 62 . . . Reagent cartridge, Buffer supply section, 66 . . . Control water tank, 68 . . . Hot-water supply water tank, 70 . . . Buffer supply pipe, 72 . . . Filtration section, 74 . . . Suction pump, 76 . . . Suction head, 78 . . . PMT section, 80 . . . Collection unit, 82 . . . Collection carrier cartridge, 82*a* . . . Upper lid, 82*b* . . . Carrier filling dish, 82*c* . . . Main body, 82*d* . . . filter, 82*e* . . . Filter fixing ring, 84 . . . Blower fan, 86 . . . Impactor nozzle head, 87 . . . Nozzle hole, 88 . . . Exhaust filer, 90 . . . Collection carrier

The invention claimed is:

1. A collection unit comprising:

a collection carrier cartridge including a carrier filling dish, provided with an inner bulkhead wall around a through hole at a center of a main plate thereof and an outer bulkhead wall around an outer portion of the main plate, where the carrier filling dish is fillable with a collection carrier between the inner and outer bulkhead walls for collecting bacteria floating in air, and an upper lid on which the carrier filling dish is placed, formed with a protrusion inserted through the through hole when collecting the bacteria floating in air, and where a nozzle for supplying solating liquid or ATP reagent is insertable through the through hole after collecting the bacteria floating in the air;

an impactor nozzle head which covers a surface of the collection carrier and has a plurality of nozzle holes facing the surface of the collection carrier; and a fan which introduces air to the surface of the collection carrier, through the nozzle holes, wherein a velocity of the air passing through the nozzle holes is 40 m/s to 50 m/s.

2. The collection unit according to claim 1, wherein among the nozzle holes, centers of adjacent nozzle holes are arranged at respective apexes of an equilateral triangle.

3. The collection unit according to claim 2, wherein the adjacent nozzle holes are arranged to have their said centers at the respective apexes of an equilateral triangle, in a plan view of the impactor nozzle head.

4. The collection unit according to claim 2, wherein the nozzle holes have a hole diameter of 0.6 mm, a hole pitch between the nozzle holes is 2.6 mm, and a distance between an opposing surface of the impactor nozzle head and a surface of the collection carrier is 1.5 mm.

5. The collection unit according to claim 3, wherein the nozzle holes have a hole diameter of 0.6 mm, a hole pitch between the nozzle holes is 2.6 mm, and a distance between an opposing surface of the impactor nozzle head and a surface of the collection carrier is 1.5 mm.

6. The collection unit according to claim 1, wherein the nozzle holes have a hole diameter of 0.6 mm, a hole pitch between the nozzle holes is 2.6 mm, and a distance between an opposing surface of the impactor nozzle head and a surface of the collection carrier is 1.5 mm.

* * * * *